(12) United States Patent
Nie et al.

(10) Patent No.: US 7,943,325 B2
(45) Date of Patent: May 17, 2011

(54) DIAGNOSIS OF FERTILITY CONDITIONS USING A SERINE PROTEASE

(75) Inventors: Guiying Nie, Glen Waverley (AU); Lois Adrienne Salamonsen, Kew (AU)

(73) Assignee: Prince Henry's Institute of Medical Research, Victoria (AU)

( * ) Notice: Subject to any disclaimer, the term of this patent is extended or adjusted under 35 U.S.C. 154(b) by 159 days.

(21) Appl. No.: 12/339,203

(22) Filed: Dec. 19, 2008

(65) Prior Publication Data

US 2009/0186367 A1    Jul. 23, 2009

Related U.S. Application Data

(60) Provisional application No. 61/015,956, filed on Dec. 21, 2007.

(51) Int. Cl.
*G01N 33/53*    (2006.01)

(52) U.S. Cl. .......................................... 435/7.1; 435/7.2

(58) Field of Classification Search .................. None
See application file for complete search history.

(56) References Cited

OTHER PUBLICATIONS

Nie et al. Biochem J. 2003 vol. 371, p. 39-48.*

* cited by examiner

*Primary Examiner* — Jacob Cheu
(74) *Attorney, Agent, or Firm* — Klauber & Jackson LLC

(57) ABSTRACT

The present invention relates to a method of diagnosing an infertility condition in a human female subject, the method comprising detecting pregnancy-related serine protease (PRSP) protein in a test sample taken from said subject at between 7 and 20 weeks into pregnancy; detecting PRSP protein in a test sample from a fertile control mammal taken within the same period; and comparing the PRSP protein in the test sample with the PRSP protein detected in the control sample, wherein a change in PRSP protein in the sample compared to the control sample is indicative of an infertility condition.

24 Claims, 10 Drawing Sheets

Figure 1. The effects of the maternal levels of the protease on fetal weight at E18. The weight of fetuses from the wild-type (+/+) mothers was significantly higher (P<0.05) than those from the heterozygous (+/-) and the homozygous (-/-) mothers.

Figure 2. The effects of the maternal levels of the protease on placenta weight at E18. The weight of placentas from the wild-type (+/+) mothers was significantly higher (P<0.05) than those from the homozygous (-/-) mothers.

Figure 3. Serum levels of the protease (the 39kDa band) at 7-9 weeks of gestation. The median level was much lower in IUGR sera compared to the normal samples (Norm) at 9 weeks.

Figure 4. Serum levels of the protease (the 39kDa band) at 9 weeks of gestation. The median level was significantly higher in PE sera compared to the normals at 9 weeks.

Figure 5. Serum levels of the protease (the 30kDa band) at 14 weeks of gestation. The median level was much lower in PE sera compared to the normals at 14 weeks.

SEQUENCE LISTING

<160> NUMBER OF SEQ ID NOS: 11

<210> SEQ ID NO 1
<211> LENGTH: 2450
<212> TYPE: DNA
<213> ORGANISM: Mus musculus

<400> SEQUENCE: 1

```
gaagctcggc tgagagaggc ccgggtcagt ccccacacca tgccctgttt gcgctccggg      60
ccagagtgcg cctgagcggt tcgggcctcg gtatccccgc gggtcttgcg ccgccgcctc     120
tccgcgatgc aggcgcgcgc gctgctcccc gccacgctgg ccattctggc cacgctggct     180
gtgttggctc tggcccggga gccccagcg gctccgtgtc ctgcgcgctg cgacgtgtcg      240
cgctgtccga gccctcgctg ccctgggggc tatgtgcctg acctctgcaa ctgctgcctg     300
gtgtgcgctg ccagcgaggg cgagccctgc ggccgccccc tggactctcc gtgcggggac     360
agtctggagt gcgtgcgcgg cgtgtgccgc tgccgttgga cccacactgt gtgtggcaca     420
gacgggcata cttatgccga cgtgtgcgcg ctgcaggccg ccagccgtcg tgcgttgcag     480
gtctccggga ctccagtgcg ccagctgcag aagggtgcct gtccctctgg tctccaccag     540
ctgaccagtc cgcggtacaa gttcaacttc atcgccgatg tggtggagaa gattgcgcca     600
gctgtggtcc acatagagct cttctctgaga caccccctgt ttggccggaa tgtgccgctg     660
tccagtggct cgggcttcat catgtcagaa gccggttga tcgtcaccaa cgcccacgtg      720
gtctccagct ccagcactgc ctccggccgg cagcagctga aggtgcagct gcagaatggg     780
gatgcctatg aggccaccat ccaggacatc gacaagaagt cggacattgc cacgattgta     840
atccacccca agaaaaagct ccctgtgttg ctgctgggtc actcagcaga cctgcggcct     900
ggcgagttcg tggtggccat cggcagcccc tttgccctgc agaacaccgt gacaacgggc     960
attgtcagca ctgcccagcg ggatggcaag agctgggtc tccgggactc agacatggac    1020
tatatccaga ccgatgccat catcaattac gggaactcag aggacccct ggtgaacctg     1080 gatggcgagg tcatcggcat caacacgctc aaggttgcag ctggcatctc ctttgccatc    1140
ccctcagatc gcatcacacg cttcctctct gagttccaaa acaagcatgt gaaagactgg    1200
aagaagcgct tcattggcat ccggatgcgg accatcacgc caagtttggt ggaggaactg    1260
aaggccgcca cccagacttt ccagcggtc agcagtggaa tatatgttca agaggtggtt    1320
cccaattcac cttctcagag aggaggcatc caagatggcg acatcatcgt caaagtcaat    1380
ggccgccccc tggcggattc cagcgagctg caggaggcag tcctgaacga gtcttcactc    1440
ctgctggagg tgcggcgagg caatgatgat ctcctcttca gcatcatccc tgaggtggtc    1500
atgtgaggct actctcatcc agtgccatgc caaagcctac agaaggtggg gttccggcct    1560
tcatgaaatc aggacaaacg gctgctgtgg tcctcagcag gatcaacagt ctcctctctg    1620
ggtccagcgc tgagtccaag gctggatcta accagggtc cggatctcag ccttgaccct      1680
taatttcagc tccagtagag gaagcacagc gtcctttgga ccagatgctc ctgatgttac    1740
cgtctgagtt ctctaggcct agaagctctt agaaacctcc ctggaagtct gcccttcccc    1800
cacccccacc ccagctttct gcctctgccc tcaggaaggc ccaccggct cccatcccac     1860 ctcttctccc ttgtatccca gtgcctcaac ctctccctgt tacaggcact ttcctgacac    1920
taccaggctt ccatctgcct cagcacaccc cacccccatg gtaagacagg ggctgcttgc    1980
cctaccaccc ggtatccctg gagggcaggc cctgtagctg tcccctggag aagccagggt    2040
cctgacctgg agcaggttaa catccctcac tgctgagctg agcctgtgc tggccaggat     2100 ggacaggaag atgagtttca taatcacgtg gtctccaacc ctgacagctc attctcccaa    2160
ggtgactaca cggtggccaa agaggagcgg acacctgcct gaggtgcaag gactgagcca    2220
cttcacctct gcatgcagtt ctgggtgcgg cagctgtctg tgaagatggc gccacccagc    2280
agccagcagg ctcccaaggg catctttgtt ctccctagtg tttcaagtgt atttgtgagc    2340
attgctgtaa agtttctccc actacccaca ttgcttgtac tgtatgtttc tctactgtat    2400
```

```
ggcattaaag tttacaagca catagctgtc aaccagaaaa aaaaaattcc          2450
```

<210> SEQ ID NO 2
<211> LENGTH: 459
<212> TYPE: PRT
<213> ORGANISM: Mus musculus

<400> SEQUENCE: 2

```
Met Gln Ala Arg Ala Leu Leu Pro Ala Thr Leu Ala Ile Leu Ala Thr
1               5                   10                  15

Leu Ala Val Leu Ala Leu Ala Arg Glu Pro Pro Ala Ala Pro Cys Pro
            20                  25                  30

Ala Arg Cys Asp Val Ser Arg Cys Pro Ser Pro Arg Cys Pro Gly Gly
        35                  40                  45

Tyr Val Pro Asp Leu Cys Asn Cys Cys Leu Val Cys Ala Ala Ser Glu
    50                  55                  60

Gly Glu Pro Cys Gly Arg Pro Leu Asp Ser Pro Cys Gly Asp Ser Leu
65                  70                  75                  80

Glu Cys Val Arg Gly Val Cys Arg Cys Arg Trp Thr His Thr Val Cys
                85                  90                  95

Gly Thr Asp Gly His Thr Tyr Ala Asp Val Cys Ala Leu Gln Ala Ala
            100                 105                 110

Ser Arg Arg Ala Leu Gln Val Ser Gly Thr Pro Val Arg Gln Leu Gln
        115                 120                 125

Lys Gly Ala Cys Pro Ser Gly Leu His Gln Leu Thr Ser Pro Arg Tyr
    130                 135                 140

Lys Phe Asn Phe Ile Ala Asp Val Val Glu Lys Ile Ala Pro Ala Val
145                 150                 155                 160

Val His Ile Glu Leu Phe Leu Arg His Pro Leu Phe Gly Arg Asn Val
                165                 170                 175

Pro Leu Ser Ser Gly Ser Gly Phe Ile Met Ser Glu Ala Gly Leu Ile
            180                 185                 190

Val Thr Asn Ala His Val Val Ser Ser Ser Thr Ala Ser Gly Arg
        195                 200                 205

Gln Gln Leu Lys Val Gln Leu Gln Asn Gly Asp Ala Tyr Glu Ala Thr
    210                 215                 220

Ile Gln Asp Ile Asp Lys Lys Ser Asp Ile Ala Thr Ile Val Ile His
225                 230                 235                 240

Pro Lys Lys Lys Leu Pro Val Leu Leu Leu Gly His Ser Ala Asp Leu
                245                 250                 255

Arg Pro Gly Glu Phe Val Val Ala Ile Gly Ser Pro Phe Ala Leu Gln
            260                 265                 270

Asn Thr Val Thr Thr Gly Ile Val Ser Thr Ala Gln Arg Asp Gly Lys
        275                 280                 285

Glu Leu Gly Leu Arg Asp Ser Asp Met Asp Tyr Ile Gln Thr Asp Ala
    290                 295                 300

Ile Ile Asn Tyr Gly Asn Ser Gly Gly Pro Leu Val Asn Leu Asp Gly
305                 310                 315                 320

Glu Val Ile Gly Ile Asn Thr Leu Lys Val Ala Ala Gly Ile Ser Phe
                325                 330                 335

Ala Ile Pro Ser Asp Arg Ile Thr Arg Phe Leu Ser Glu Phe Gln Asn
            340                 345                 350

Lys His Val Lys Asp Trp Lys Lys Arg Phe Ile Gly Ile Arg Met Arg
        355                 360                 365
```

| | | | | | | | | | | | | |
|---|---|---|---|---|---|---|---|---|---|---|---|---|
|Thr|Ile|Thr|Pro|Ser|Leu|Val|Glu|Glu|Leu|Lys|Ala|Ala|Asn|Pro|Asp|
| |370| | | |375| | | |380| | | | | | |
|Phe|Pro|Ala|Val|Ser|Ser|Gly|Ile|Tyr|Val|Gln|Glu|Val|Val|Pro|Asn|
|385| | | | |390| | | |395| | | | |400| |
|Ser|Pro|Ser|Gln|Arg|Gly|Gly|Ile|Gln|Asp|Gly|Asp|Ile|Ile|Val|Lys|
| | | | |405| | | |410| | | | |415| | |
|Val|Asn|Gly|Arg|Pro|Leu|Ala|Asp|Ser|Ser|Glu|Leu|Gln|Glu|Ala|Val|
| | | |420| | | | |425| | | | |430| | |
|Leu|Asn|Glu|Ser|Ser|Leu|Leu|Leu|Glu|Val|Arg|Arg|Gly|Asn|Asp|Asp|
| | | |435| | | |440| | | | |445| | | |
|Leu|Leu|Phe|Ser|Ile|Ile|Pro|Glu|Val|Val|Met| | | | | |
| |450| | | | |455| | | | | | | | | |

<210> SEQ ID NO 3
<211> LENGTH: 2543
<212> TYPE: DNA
<213> ORGANISM: Homo sapiens

<400> SEQUENCE: 3

```
gtgcgctccc tgcgccctgg ggatgcccct gccgccctga cgcccgccag cctgagccac      60
cggcgcatgt gaccgcgcgt ccgccccagt cccatccgta ggcgcccggc gcccggcccc     120
gcagcggcct cgttgtcccc gccggccccc gccggtctc ccgcgctgcc acccgccgcc     180
ggccctgccg ccatgcaggc gcgagcgctg ctcctggccg cgttggccgc gctggcgctg     240
gcccgggagc ccctgcggc gccgtgtccc gcgcgctgcg acgtgtcgcg gtgtcccagc     300
ccccgctgcc ccggcggcta cgtgcccgac tctgcaact gctgcctggt gtgcgccgcc     360
agcgagggcg agccctgtgg cggccctctg gactcgcctt cgggcgagag cctggagtgc     420
gtgcgcggcc tatgccgctg ccgctggtcg cacgccgtgt gtggcaccga cgggcacacc     480
tatgccaacg tgtgcgcgct gcaggcggcc agccgccgcg cgctgcagct ctccgggacg     540
cccgtgcgcc agctgcagaa gggcgcctgc ccgttgggtc tccaccagct gagcagcccg     600
cgctacaagt tcaacttcat tgctgacgtg gtggagaaga tcgcaccagc cgtggtccac     660
atagagctct tcctgagaca cccgctgttt ggccgcaacg tgcccctgtc cagcggttct     720
ggcttcatca tgtcagaggc cggcctgatc atcaccaatg cccacgtggt gtccagcaac     780
agtgctgccc cgggcaggca gcagctcaag gtgcagctac agaatgggga ctcctatgag     840
gccaccatca agacatcgaa caagaagtcg acattgcca ccatcaagat ccatcccaag     900
aaaaagctcc ctgtgttgtt gctgggtcac tcggccgacc tgcggcctgg ggagtttgtg     960
gtggccatcg gcagtccctt cgccctacag aacacagtga caacgggcat cgtcagcact    1020
gcccagcggg agggcaggga gctgggcctc cgggactccg acatggacta catccagacg    1080
gatgccatca tcaactacgg gaactccggg ggaccactgg tgaacctgga tggcgaggtc    1140
attggcatca acacgctcaa ggtcacggct ggcatctcct tgccatccc ctcagaccgc    1200
atcacacggt tcctcacaga gttccaagac aagcagatca agactggaa gaagcgcttc    1260
atcggcatac ggatgcggac gatcacacca agcctggtgg atgagctgaa ggccagcaac    1320
ccggacttcc cagaggtcag cagtggaatt tatgtgcaag aggttgcgcc gaattcacct    1380
tctcagagag gcggcatcca agatggtgac atcatcgtca aggtcaacgg gcgtcctcta    1440
gtggactcga gtgagctgca ggaggccgtg ctgaccgagt ctcctctcct actggaggtg    1500
cggcggggga acgacgacct cctcttcagc atcgcacctg aggtggtcat gtgagggggcg    1560
cattcctcca gcgccaagcg tcagagcctg cagacaacgg agggcagcgc ccccccgaga    1620
```

```
tcaggacgaa ggaccaccgt cggtcctcag cagggcggca gcctcctcct ggctgtccgg      1680
ggcagagcgg aggctgggct tggccagggg cccgaatttc cgcctgggga gtgttggatc      1740
cacatcccgg tgccggggag ggaagcccaa catcccttg tacagatgat cctgaaagtc       1800
acttccaagt tctccggata ttcacaaaac tgccttccat ggaggtcccc tcctctccta      1860
gcttcccgcc tctgcccctg tgaacaccca tctgcagtat cccctgctcc tgcccctcct      1920
actgcaggtc tgggctgcca agcttcttcc cccctgacaa acgcccacct gacctgaggc      1980
cccagcttcc ctctgcccta ggacttacca agctgtaggg ccagggctgc tgcctgccag      2040
cctggggtcc ctggaggaca ggtcacatct gatcccttg gggtgcgggg gtggggtcca      2100
gcccagagca ggcactgagt gaatgccccc tggctgcgga gctgagcccc gccctgccat      2160
gaggttttcc tccccaggca ggcaggaggc gcgggggagc acgtggaaag ttggctgctg      2220
cctggggaag cttctcctcc ccaaggcggc catggggcag cctgcagagg acagtggacg      2280
tggagctgcg gggtgtgagg actgagccgg cttccccttc ccacgcagct ctgggatgca      2340
gcagccgctc gcatggaagt gccgcccaga ggcatgcagg ctgctgggca ccaccccctc      2400
atccagggaa cgagtgtgtc tcaaggggca tttgtgagct ttgctgtaaa tggattccca      2460
gtgttgcttg tactgtatgt ttctctactg tatggaaaat aaagtttaca agcacacggt      2520
tctcaaaaaa aaaaaaaaaa aaa                                              2543

<210> SEQ ID NO 4
<211> LENGTH: 1953
<212> TYPE: DNA
<213> ORGANISM: Homo sapiens

<400> SEQUENCE: 4
ccagtcccat ccgtaggcgc ccggcgcccg gccccgcagc ggcctcgttg tccccgccgg        60
cccccgcccg gtctcccgcg ctgccacccg ccgccggccc tgccgccatg caggcgcgag       120
cgctgctcct ggccgcgttg gccgcgctgg cgctggcccg ggagcccccct gcggcgccgt      180 gtcccgcgcg ctgcgacgtg tcgcggtgtc ccagccccg ctgccccggc ggctacgtgc       240
ccgacctctg caactgctgc ctggtgtgcg ccgccagcga gggcgagccc tgtggcggcc       300
ctctggactc gccttgcggc gagagcctgg agtgcgtgcg cggcctatgc gctgccgct       360 ggtcgcacgc cgtgtgtggc accgacgggc acacctatgc caacgtgtgc gcgctgcagg      420
cggccagccg ccgcgcgctg cagctctccg ggacgcccgt gcgccagctg cagaagggcg      480
cctgcccgtt gggtctccac cagctgagca gcccgcgcta caagttcaac ttcattgctg      540
acgtggtgga gaagatcgca ccagccgtgg tccacataga gctcttcctg agacacccgc      600
tgtttggccg caacgtgccc ctgtccagcg gttctggctt catcatgtca gaggccggcc      660
tgatcatcac caatgcccac gtggtgtcca gcaacagtgc tgccccgggc aggcagcagc      720
tcaaggtgca gctacagaat ggggactcct atgaggccac catcaaagac atcgacaaga      780
agtcggacat tgccaccatc aagatccatc caagaaaaa gctccctgtg ttgttgctgg      840
gtcactcggc cgacctgcgg cctggggagt ttgtggtggc catcggcagt cccttcgccc      900
tacagaacac agtgacaacg ggcatcgtca gcactgccca gcgggagggc agggagctgg      960
gcctccggga ctccgacatg gactacatcc agacggatgc catcatcaac tacgggaact      1020 cgggggacc actggtgaac ctggatggcg aggtcattgg catcaacacg ctcaaggtca      1080
cggctggcat ctccttccc atcccctcag accgcatcac acggttcctc acagagttcc      1140
aagacaagca gatcaaagcc ccctcactgg cagttcattg agagcagggg gcttcctcac      1200
```

-continued

```
gtttcccccct cctccatgac cccgtcagcc aagcacatgg accccagtgc agccaaggct   1260
ggtgccatga gggctggtca catgaagagc tgctgttgag gatgccgcca ttgttcttct   1320
gtgtccatta tgggaagaca atctggagcc aggcagagcc tgtctttccc aaagaagctg   1380
aagtcttctt ctcttgaaca gtggggacca tctaatctct tgagccctt tcctgttggc    1440 ttctaggaag ctcagagcta gattcagggg tgcacccaga cctgtcctag catgctcctt   1500
tccctaatga ccgagtcttt cctgttgaat tatcccattc tccatgggtg cctttgactt   1560
tggcctcctt actggaaatt agcggagctg ctgtttgcac acactgagct gtgaggtggc   1620
tttccttgga agtggatgat agtgtcctct tcccttcttg cctctctctt tctcctgaga   1680
caggatcccc ctggggccta ggtttgctcc tttgttgtac aggggctgtc ccagttagtg   1740
ctgacctcat cccagaaccc cctgggaaat atcccctgtc ctcagagctg tgtcccctcc   1800
ccaaggacag tgcagactaa ctgaggagcc tgataaacct tagctgcatg gcacacttgc   1860
aattttaaaa tccttctgaa gttgactggt gtttgtactt gcttctcttt tttatttaat   1920
aaaatccaat gatccaaaaa aaaaaaaaaa aaa                                1953
```

<210> SEQ ID NO 5
<211> LENGTH: 453
<212> TYPE: PRT
<213> ORGANISM: Homo sapiens

<400> SEQUENCE: 5

```
Met Gln Ala Arg Ala Leu Leu Ala Ala Leu Ala Ala Leu Ala Leu
1               5                   10                  15

Ala Arg Glu Pro Pro Ala Ala Pro Cys Pro Ala Arg Cys Asp Val Ser
                20                  25                  30

Arg Cys Pro Ser Pro Arg Cys Pro Gly Gly Tyr Val Pro Asp Leu Cys
            35                  40                  45

Asn Cys Cys Leu Val Cys Ala Ala Ser Glu Gly Glu Pro Cys Gly Gly
        50                  55                  60

Pro Leu Asp Ser Pro Cys Gly Glu Ser Leu Glu Cys Val Arg Gly Leu
65                  70                  75                  80

Cys Arg Cys Arg Trp Ser His Ala Val Cys Gly Thr Asp Gly His Thr
                85                  90                  95

Tyr Ala Asn Val Cys Ala Leu Gln Ala Ala Ser Arg Arg Ala Leu Gln
                100                 105                 110

Leu Ser Gly Thr Pro Val Arg Gln Leu Gln Lys Gly Ala Cys Pro Leu
            115                 120                 125

Gly Leu His Gln Leu Ser Ser Pro Arg Tyr Lys Phe Asn Phe Ile Ala
        130                 135                 140

Asp Val Val Glu Lys Ile Ala Pro Ala Val Val His Ile Glu Leu Phe
145                 150                 155                 160

Leu Arg His Pro Leu Phe Gly Arg Asn Val Pro Leu Ser Ser Gly Ser
                165                 170                 175

Gly Phe Ile Met Ser Glu Ala Gly Leu Ile Ile Thr Asn Ala His Val
                180                 185                 190

Val Ser Ser Asn Ser Ala Ala Pro Gly Arg Gln Gln Leu Lys Val Gln
            195                 200                 205

Leu Gln Asn Gly Asp Ser Tyr Glu Ala Thr Ile Lys Asp Ile Asp Lys
        210                 215                 220

Lys Ser Asp Ile Ala Thr Ile Lys Ile His Pro Lys Lys Lys Leu Pro
225                 230                 235                 240

Val Leu Leu Leu Gly His Ser Ala Asp Leu Arg Pro Gly Glu Phe Val
```

```
                    245                 250                 255
Val Ala Ile Gly Ser Pro Phe Ala Leu Gln Asn Thr Val Thr Thr Gly
                260                 265                 270

Ile Val Ser Thr Ala Gln Arg Glu Gly Arg Glu Leu Gly Leu Arg Asp
            275                 280                 285

Ser Asp Met Asp Tyr Ile Gln Thr Asp Ala Ile Ile Asn Tyr Gly Asn
        290                 295                 300

Ser Gly Gly Pro Leu Val Asn Leu Asp Gly Glu Val Ile Gly Ile Asn
305                 310                 315                 320

Thr Leu Lys Val Thr Ala Gly Ile Ser Phe Ala Ile Pro Ser Asp Arg
                325                 330                 335

Ile Thr Arg Phe Leu Thr Glu Phe Gln Asp Lys Gln Ile Lys Asp Trp
            340                 345                 350

Lys Lys Arg Phe Ile Gly Ile Arg Met Arg Thr Ile Thr Pro Ser Leu
        355                 360                 365

Val Asp Glu Leu Lys Ala Ser Asn Pro Asp Phe Pro Glu Val Ser Ser
    370                 375                 380

Gly Ile Tyr Val Gln Glu Val Ala Pro Asn Ser Pro Ser Gln Arg Gly
385                 390                 395                 400

Gly Ile Gln Asp Gly Asp Ile Ile Val Lys Val Asn Gly Arg Pro Leu
                405                 410                 415

Val Asp Ser Ser Glu Leu Gln Glu Ala Val Leu Thr Glu Ser Pro Leu
            420                 425                 430

Leu Leu Glu Val Arg Arg Gly Asn Asp Asp Leu Leu Phe Ser Ile Ala
        435                 440                 445

Pro Glu Val Val Met
    450

<210> SEQ ID NO 6
<211> LENGTH: 357
<212> TYPE: PRT
<213> ORGANISM: Homo sapiens

<400> SEQUENCE: 6

Met Gln Ala Arg Ala Leu Leu Leu Ala Ala Leu Ala Ala Leu Ala Leu
1               5                   10                  15

Ala Arg Glu Pro Pro Ala Ala Pro Cys Pro Ala Arg Cys Asp Val Ser
                20                  25                  30

Arg Cys Pro Ser Pro Arg Cys Pro Gly Gly Tyr Val Pro Asp Leu Cys
            35                  40                  45

Asn Cys Cys Leu Val Cys Ala Ala Ser Glu Gly Glu Pro Cys Gly Gly
        50                  55                  60

Pro Leu Asp Ser Pro Cys Gly Glu Ser Leu Glu Cys Val Arg Gly Leu
65                  70                  75                  80

Cys Arg Cys Arg Trp Ser His Ala Val Cys Gly Thr Asp Gly His Thr
                85                  90                  95

Tyr Ala Asn Val Cys Ala Leu Gln Ala Ala Ser Arg Arg Ala Leu Gln
                100                 105                 110

Leu Ser Gly Thr Pro Val Arg Gln Leu Gln Lys Gly Ala Cys Pro Leu
            115                 120                 125

Gly Leu His Gln Leu Ser Ser Pro Arg Tyr Lys Phe Asn Phe Ile Ala
        130                 135                 140

Asp Val Val Glu Lys Ile Ala Pro Ala Val Val His Ile Glu Leu Phe
145                 150                 155                 160

Leu Arg His Pro Leu Phe Gly Arg Asn Val Pro Leu Ser Ser Gly Ser
```

```
                    165                 170                 175
Gly Phe Ile Met Ser Glu Ala Gly Leu Ile Ile Thr Asn Ala His Val
            180                 185                 190
Val Ser Ser Asn Ser Ala Ala Pro Gly Arg Gln Gln Leu Lys Val Gln
            195                 200                 205
Leu Gln Asn Gly Asp Ser Tyr Glu Ala Thr Ile Lys Asp Ile Asp Lys
            210                 215                 220
Lys Ser Asp Ile Ala Thr Ile Lys Ile His Pro Lys Lys Lys Leu Pro
225                 230                 235                 240
Val Leu Leu Leu Gly His Ser Ala Asp Leu Arg Pro Gly Glu Phe Val
                245                 250                 255
Val Ala Ile Gly Ser Pro Phe Ala Leu Gln Asn Thr Val Thr Thr Gly
            260                 265                 270
Ile Val Ser Thr Ala Gln Arg Glu Gly Arg Glu Leu Gly Leu Arg Asp
            275                 280                 285
Ser Asp Met Asp Tyr Ile Gln Thr Asp Ala Ile Ile Asn Tyr Gly Asn
            290                 295                 300
Ser Gly Gly Pro Leu Val Asn Leu Asp Gly Glu Val Ile Gly Ile Asn
305                 310                 315                 320
Thr Leu Lys Val Thr Ala Gly Ile Ser Phe Ala Ile Pro Ser Asp Arg
                325                 330                 335
Ile Thr Arg Phe Leu Thr Glu Phe Gln Asp Lys Gln Ile Lys Ala Pro
                340                 345                 350
Ser Leu Ala Val His
        355

<210> SEQ ID NO 7
<211> LENGTH: 1897
<212> TYPE: DNA
<213> ORGANISM: Mus musculus

<400> SEQUENCE: 7
gaagctcggc tgagagaggc ccgggtcagt ccccacacca tgccctgttt gcgctccggg      60
ccagagtgcg cctgagcggt tcgggcctcg gtatccccgc gggtcttgcg ccgccgcctc     120
tccgcgatgc aggcgcgcgc gctgctcccc gccacgctgg ccattctggc cacgctggct     180
gtgttggctc tggcccggga gcccccagcg gctccgtgtc ctgcgcgctg cgacgtgtcg     240
cgctgtccga gccctcgctg ccctgggggc tatgtgcctg acctctgcaa ctgctgcctg     300
gtgtgcgctg ccagcgaggg cgagccctgc ggccgcccc tggactctcc gtgcggggac     360
agtctggagt gcgtgcgcgg cgtgtgccgc tgccgttgga cccacactgt gtgtggcaca     420
gacgggcata cttatgccga cgtgtgcgcg ctgcaggccg ccagccgtcg tgcgttgcag     480
gtctccggga ctccagtgcg ccagctgcag aagggtgcct gtccctctgg tctccaccag     540
ctgaccagtc gcggtacaa gttcaacttc atcgccgatg tggtggagaa gattgcgcca     600
gctgtggtcc acatagagct ctttctgaga caccccctgt ttggccggaa tgtgccgctg     660
tccagtggct cgggcttcat catgtcagaa gccggtttga tcgtcaccaa cgcccacgtg     720
gtctccagct ccagcactgc ctccggccgg cagcagctga aggtgcagct gcagaatggg     780
gatgcctatg aggccaccat ccaggacatc gacaagaagt cggacattgc cacgattgta     840
atccacccca agaaaaagct ccctgtgttg ctgctgggtc actcagcaga cctgcggcct     900
ggcgagttcg tggtggccat cggcagcccc tttgccctgc agaacaccgt gacaacgggc     960
attgtcagca ctgcccagcg ggatggcaag gagctgggtc tccgggactc agacatggac    1020
```

```
tatatccaga ccgatgccat catcaattac gggaactcag gaggacccct ggtgaacctg   1080
gatggcgagg tcatcggcat caacacgctc aaggttgcag ctggcatctc ctttgccatc   1140
ccctcagatc gcatcacacg cttcctctct gagttccaaa acaagcatgt gaaagccctc   1200
tcaccagcac tgcactgaga gcaggggcct tcctcctgct tgcccctcc tttgcggccc    1260 tgccagccac acacaaggac cccagtacag ccaagactgg tcccatgaag aactgcaacc   1320
gaggagcctc gttctgttcc aagtggccct atatgaagat acaggagca ggcagagcct    1380 gtcccttcca ggaatccgag acaccttctg gtgaatagtg ggaactagct gccttttctc   1440
ttggccggta ggaagctcag aactagacca gggttcctag accattggta gccttggctc   1500
tttgtctagt ggccagggct ttccagttta gcttgtttat ggggtcggaa caccacccac   1560
atacactggc ctatgggtga ttactgtgct ggaaatgggc cagcggcctt ttgtccccta   1620
gctgtctcat cttttctcag acaagaagtc cccggggcag gatctgctcc tctgtggcag   1680
agcaactatc ctagtcacag tgacctggtc actcagcctg ggctctgcgg aaatgctcac   1740
acccatccca gagttatgtt atcacccaag gacagtgctt acctactaca gagggtctg    1800 acgaggctta gctaagtggg gtccattgac ttaaagtcct tctgaaattt gtgcttattt   1860 atgctttttcc atttttaaat aaaaacatca gatgatc                           1897
```

<210> SEQ ID NO 8
<211> LENGTH: 363
<212> TYPE: PRT
<213> ORGANISM: Mus musculus

<400> SEQUENCE: 8

Met Gln Ala Arg Ala Leu Leu Pro Ala Thr Leu Ala Ile Leu Ala Thr
1               5                   10                  15

Leu Ala Val Leu Ala Leu Ala Arg Glu Pro Ala Ala Pro Cys Pro
            20                  25                  30

Ala Arg Cys Asp Val Ser Arg Cys Pro Ser Pro Arg Cys Pro Gly Gly
        35                  40                  45

Tyr Val Pro Asp Leu Cys Asn Cys Cys Leu Val Cys Ala Ala Ser Glu
    50                  55                  60

Gly Glu Pro Cys Gly Arg Pro Leu Asp Ser Pro Cys Gly Asp Ser Leu
65                  70                  75                  80

Glu Cys Val Arg Gly Val Cys Arg Cys Arg Trp Thr His Thr Val Cys
                85                  90                  95

Gly Thr Asp Gly His Thr Tyr Ala Asp Val Cys Ala Leu Gln Ala Ala
            100                 105                 110

Ser Arg Arg Ala Leu Gln Val Ser Gly Thr Pro Val Arg Gln Leu Gln
        115                 120                 125

Lys Gly Ala Cys Pro Ser Gly Leu His Gln Leu Thr Ser Pro Arg Tyr
    130                 135                 140

Lys Phe Asn Phe Ile Ala Asp Val Val Glu Lys Ile Ala Pro Ala Val
145                 150                 155                 160

Val His Ile Glu Leu Phe Leu Arg His Pro Leu Phe Gly Arg Asn Val
                165                 170                 175

Pro Leu Ser Ser Gly Ser Gly Phe Ile Met Ser Glu Ala Gly Leu Ile
            180                 185                 190

Val Thr Asn Ala His Val Val Ser Ser Ser Thr Ala Ser Gly Arg
        195                 200                 205

Gln Gln Leu Lys Val Gln Leu Gln Asn Gly Asp Ala Tyr Glu Ala Thr
    210                 215                 220

```
Ile Gln Asp Ile Asp Lys Lys Ser Asp Ile Ala Thr Ile Val Ile His
225                 230                 235                 240

Pro Lys Lys Lys Leu Pro Val Leu Leu Leu Gly His Ser Ala Asp Leu
                245                 250                 255

Arg Pro Gly Glu Phe Val Val Ala Ile Gly Ser Pro Phe Ala Leu Gln
            260                 265                 270

Asn Thr Val Thr Thr Gly Ile Val Ser Thr Ala Gln Arg Asp Gly Lys
        275                 280                 285

Glu Leu Gly Leu Arg Asp Ser Asp Met Asp Tyr Ile Gln Thr Asp Ala
        290                 295                 300

Ile Ile Asn Tyr Gly Asn Ser Gly Gly Pro Leu Val Asn Leu Asp Gly
305                 310                 315                 320

Glu Val Ile Gly Ile Asn Thr Leu Lys Val Ala Ala Gly Ile Ser Phe
            325                 330                 335

Ala Ile Pro Ser Asp Arg Ile Thr Arg Phe Leu Ser Glu Phe Gln Asn
            340                 345                 350

Lys His Val Lys Ala Leu Ser Pro Ala Leu His
            355                 360

<210> SEQ ID NO 9
<211> LENGTH: 11
<212> TYPE: PRT
<213> ORGANISM: artificial sequence
<220> FEATURE:
<223> OTHER INFORMATION: Antigenic peptide from mouse uterine
      protease

<400> SEQUENCE: 9

Pro Ser Gly Leu His Gln Leu Thr Ser Pro Cys
1               5                   10

<210> SEQ ID NO 10
<211> LENGTH: 12
<212> TYPE: PRT
<213> ORGANISM: artificial sequence
<220> FEATURE:
<223> OTHER INFORMATION: Antigenic peptide from mouse uterine
      protease

<400> SEQUENCE: 10

Ala Leu Gln Val Ser Gly Thr Pro Val Arg Gln Cys
1               5                   10

<210> SEQ ID NO 11
<211> LENGTH: 13
<212> TYPE: PRT
<213> ORGANISM: artificial sequence
<220> FEATURE:
<223> OTHER INFORMATION: Antigenic peptide from region common to both
      isoforms of mouse uterine protease

<400> SEQUENCE: 11

Gly Pro Leu Val Asn Leu Asp Gly Glu Val Ile Gly Cys
1               5                   10
```

DIAGNOSIS OF FERTILITY CONDITIONS USING A SERINE PROTEASE

RELATED APPLICATION

The present application claims the priority of provisional application U.S. Ser. No. 61/015,956, filed Dec. 21, 2007. The disclosure of the aforementioned application is incorporated by reference herein in its entirety, and applicants claim the benefits of this application under 35 U.S.C. §119(e).

FIELD OF THE INVENTION

This invention relates to the evaluation of fertility and monitoring of early pregnancy, fetal development, placental development and function, parturition, and conditions such as pre-eclampsia, intrauterine growth restriction (IUGR), early abortion and abnormal uterine bleeding using a protease.

BACKGROUND OF THE INVENTION

Embryo implantation, the process by which the blastocyst attaches and implants in the uterus, leads to the establishment of an intimate relationship between the embryo and the endometrium. Implantation is one of the most important limiting factors in establishing a successful pregnancy. It is a complex process involving active interactions between the blastocyst and the uterus. The uterus must undergo dramatic morphological and physiological changes to transform itself from a non-receptive to a receptive state. This differentiation process is largely mediated by the coordinated effects of the ovarian hormones, which act through their intracellular receptors to regulate gene expression, and hence to influence cellular proliferation and differentiation. It is also regulated by the blastocyst.

While the details of the exact molecular events occurring in the uterus during this differentiation process towards receptivity are still unknown, in principle it can be predicted that a unique set of genes is up- or down-regulated in a temporally and spatially specific manner. Indeed, induction of specific genes in the uterus during the peri-implantation period, including those encoding some growth factors and cytokines, has been reported. However, given the complexity and the as-yet imprecisely defined molecular mechanism of the process, many other molecules critical for implantation are still unidentified.

In their earlier application U.S. Ser. No. 10/485,313 (which is herein incorporated in its entirety by reference) the inventors used the mouse as a model in a search for molecules important in the early stage of implantation. In the mouse on day 4.5 of pregnancy (vaginal plug=day 0), the uterus undergoes dramatic morphological changes in association with cell proliferation and differentiation, leading to the acquisition of a receptive state. This uterine remodeling is associated with an increase in vascular permeability at implantation sites. The inventors hypothesized that the proliferation and differentiation of endometrial cells at this time is associated with up- or down-regulation of a number of genes.

To identify uterine genes which are potentially critical for uterine receptivity, the inventors used the technique of RNA differential display (DDPCR) and compared the mRNA expression patterns of implantation and interimplantation sites on day 4.5 of pregnancy (Nie G, Li Y, Batten L, Griffiths B, Wang J, Findlay J & Salamonsen L A (2000) Uterine expression of alternatively spliced mRNAs of mouse splicing factor SC35 during early pregnancy. Mol. Hum. Reprod. 6: 1131-1139). One of the mRNA molecules identified as being differently regulated between the two sites was found to encode a protein molecule, with a predicted serine protease motif. This protein was significantly homologous to SEQ ID NO: 3 described in WO 00/39149 (Barnes), and had significant homology to HtrA type proteins. These proteins were not previously suggested to be involved in embryo implantation.

Accordingly, further work was performed to identify the role of this protein in pregnancy and to identify potential uses. The cDNA encoding this protein was isolated, and its uterine expression during early pregnancy in the mouse examined; the protein is up-regulated in the pregnant mouse uterus from day 4.5 and further increased in the implantation site (including the maternal deciduum and the fetus and the placenta) from day 8.5 onwards. The observed expression pattern indicated a role for this protein in implantation, placentation and early pregnancy.

It is an aim of a preferred embodiment of the present invention to further study the role of serine proteases in fertility and to develop tools for such study. It is also an aim of a preferred embodiment of the invention to provide a test for fertility related disorders.

SUMMARY OF THE INVENTION

In a first aspect the invention provides a method of diagnosing an infertility condition in a human female subject, the method comprising
(a) detecting pregnancy-related serine protease (PRSP) protein in a test sample taken from said subject at between 8 and 20 weeks into pregnancy;
(b) detecting PRSP protein in a control sample from a fertile control human female taken at the same number of weeks into pregnancy in the control as the sample taken from the subject; and
(c) comparing the PRSP protein in the test sample with the PRSP protein detected in the control sample, in which a change in the PRSP protein in the test sample compared to the control sample is indicative of an infertility condition.

In an embodiment of the first aspect, the infertility condition is an inability to achieve or sustain embryo implantation, or an inability to sustain a normal pregnancy, such as early abortion, or an insufficiency of placentation, such as pre-eclampsia or IUGR.

In another embodiment of the first aspect, the PRSP protein has a sequence selected from the group consisting of the sequences set out in SEQ ID NO:2, 5, 6 or 8.

In another embodiment of the first aspect, the PRSP protein is detected using an antibody. In one embodiment the antibody is raised against a sequence specific for PRSP, such as SEQ ID NO:10, or amino acids 133 to 142 or 116 to 126 of SEQ ID NO:2.

In another embodiment of the first aspect, the biological sample is a sample of a biological fluid, such as plasma, serum, uterine or bladder washings, or amniotic fluid or a tissue or cellular sample or extract thereof, such as placental or uterine tissue.

In another embodiment of the first aspect, PRSP protein in the test and, or control samples is indicated by a 39 kDa PRSP band on Western blot using an antibody raised against SEQ ID NO: 10.

In another embodiment of the first aspect, PRSP protein in the test and, or control sample is indicated by a 30 kDa band on Western blot using an antibody raised against SEQ ID NO: 10 when the test and control samples are taken at between 13 and 20 weeks into pregnancy.

In another embodiment of the first aspect, the change in PRSP protein is indicated by a decrease in the density of the 39 kDa PRSP band, indicative of IUGR.

In another embodiment of the first aspect, the change in PRSP protein is indicated by an increase in the density of the 39 kDa PRSP band, indicative of pre-eclampsia.

In another embodiment of the first aspect, the change in PRSP protein is indicated by a decrease in density of the 30 kDa band, indicative of pre-eclampsia.

In their earlier application U.S. Ser. No. 10/485,313 (PCT/AU02/01010) the inventors described isoforms of a serine protease whose expression is upregulated at the site of embryo implantation during early pregnancy. This enzyme was described as a pregnancy related serine protease, or PRSP. It was proposed that this protein could be used in an assay to diagnose infertility conditions.

Several sequences for serine proteases upregulated at the site of embryo implantation during early pregnancy have been identified and these have substantial sequence homology to proteins of the HtrA family. Suitable PRSP proteins and nucleic acid molecules encoding them are provided as SEQ ID Nos: 1-8.

The inventors have now determined the timing of the upregulation in expression of this protein in a normal pregnancy and accordingly have identified the key time points between which any sample should be taken to assay for the serine protease to diagnose infertility conditions. From experimental evidence, the best time to take a sample upon which to assay for PRSP is 8-20 weeks, with the period between 8-14, 8-10 and 8-9, or 13-14 weeks being particularly preferred. Tests performed on samples taken at 9 weeks into pregnancy have been shown to be able to diagnose between IUGR and pre-eclampsia.

In a second aspect the invention provides a null mouse model in which expression of serine protease genes having SEQ ID NO:1 and 7 and therefore serine protease proteins having SEQ ID NO: 2 or 8, is blocked. Preferably, the null mouse has the genes having SEQ ID NO: 1 and or 7 deleted.

In a third aspect the invention provides an antibody raised against a peptide comprising SEQ ID NO: 10.

In a fourth aspect the invention provides an antibody raised against a peptide having SEQ ID NO: 10.

In a fifth aspect the invention provides the use of the antibody of the third aspect in the method of the first aspect.

In a sixth aspect the invention provides the use of the antibody of the fourth aspect in the method of the first aspect.

DETAILED DESCRIPTION

Figure 1:
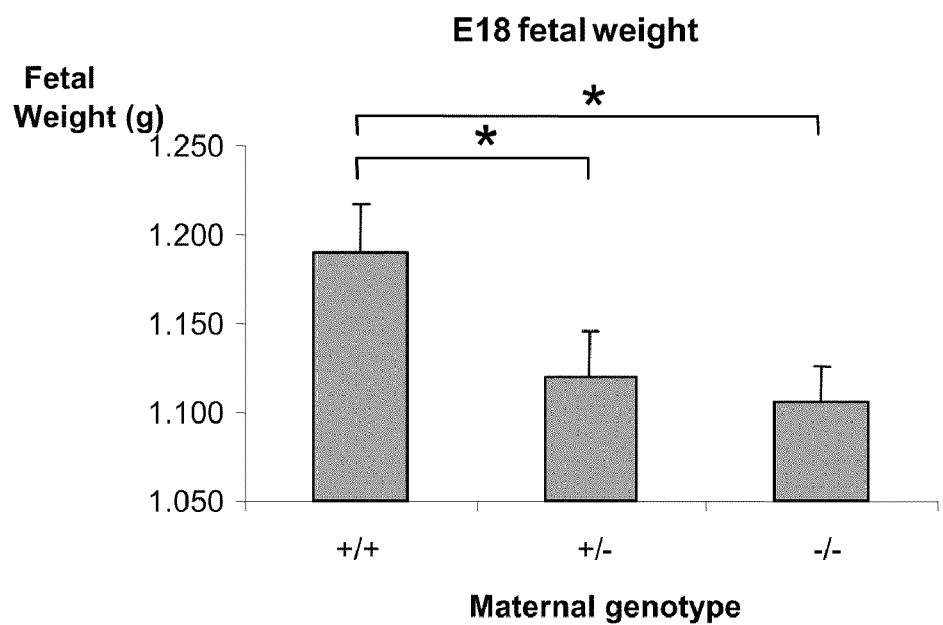
FIG. 1 shows the effects of maternal levels of the protease on fetal weight at E18.

The first aspect of the invention involves assaying a test sample for PRSP.

The assay may be for a nucleic acid molecule encoding the PRSP protein or for the protein per se.

The serine protease encoding nucleic acid molecule may be a cDNA, a genomic DNA, or an RNA, and may be in the sense or the anti-sense orientation. Preferably the nucleic acid molecule is a cDNA.

Preferably the PRSP nucleic acid molecule has a sequence selected from the group consisting of
(a) a cDNA molecule having the sequence set out in SEQ ID NO:1, 3, 4 or 7;
(b) a nucleic acid molecule which is able to hybridize under at least moderately stringent conditions to the molecule of (a); and
(c) a nucleic acid molecule which has at least 75% sequence identity to the molecule of (a).

More preferably in (b) the nucleic acid molecule is able to hybridize under stringent conditions to the molecule of (a). More preferably in (c) the nucleic acid molecule has at least 80%, even more preferably at least 90% sequence identity to the molecule of (a).

Probes or primers specific for PRSP nucleic acid may be utilized. These may have a minimum of 10 contiguous bases specific for a PRSP sequence, preferably selected from SEQ ID NO: 1, 3, 4 or 7.

Persons skilled in the art would be able to identify how to assay for PRSP nucleic acid in a test sample.

Preferably the PRSP protein has a sequence selected from the group consisting of the sequences set out in SEQ ID NO:2, 5, 6 or 8; more preferably the sequence is the one set out in SEQ ID NO:5 or SEQ ID NO:6.

Persons skilled in the art would be able to identify how to assay for PRSP protein in a test sample.

In an embodiment the invention provides a method of detecting, diagnosing, or monitoring an infertility condition, comprising the step of using a nucleic acid molecule probe comprising at least about 15 contiguous nucleotides unique to a PRSP, as a probe in a hybridization assay performed on a biological sample from a mammal suspected to be suffering from such a condition.

The test sample may be a sample of a biological fluid such as plasma, serum, uterine or bladder washings, or amniotic fluid, or may be a tissue or cell sample or an extract thereof, for example placental or uterine tissue.

Infertility conditions as described herein include those caused by inability to achieve or sustain embryo implantation or to sustain a normal pregnancy to full term. A normal pregnancy is a pregnancy that runs to full term without the need for medical intervention.

Infertility as used herein includes disorders such as pre-eclampsia and intrauterine growth restriction (IUGR), which may provide healthy offspring, but do involve complications with pregnancy and also includes conditions such as early abortion and abnormal uterine bleeding.

Peptides specific for PRSP may be utilized as a target in the assay. These may have a minimum of 6 contiguous amino acids specific for a PRSP sequence, preferably selected from SEQ ID NO: 2, 5, 6 or 8. Peptides having 10, 20, 30, 50 or 100 residues are particularly targeted.

In one embodiment of the invention, total RNA in a sample of placental or uterine tissue from the mammal is assayed for the presence of serine protease messenger RNA, wherein an alteration in the amount of PRSP messenger RNA compared to a control measurement is indicative of impaired fertility or of impending miscarriage.

The method may utilize an antibody directed against the serine protease or a specific fragment thereof. The antibody may be polyclonal or monoclonal, and is preferably monoclonal. The antibody may suitably be directed against one of the following segments of the mouse protease:
1. Amino acids 133-142; sequence PSGLHQLTSPC (SEQ ID NO: 9).
2. Amino acids 116-126; sequence ALQVSGTPVRQC (SEQ ID NO: 10).
3. A sequence common to both isoforms, represented by amino acids 133-142 of SEQ ID NO:26; sequence GPLVNLDGEVIGC (SEQ ID NO:11).

These mouse sequences are highly homologous to corresponding regions of the human protein.

More preferably the antibody is directed to an epitope within the common region of the two isoforms disclosed herein for mouse or human PRSP. The antibody may be used to detect the serine protease in biological fluids or in tissues, cells or extracts thereof.

PRSP or fragments thereof may be used as an immunogen to generate specific anti-PRSP antibodies which can in turn be used to detect PRSP in a test or control sample. Such antibodies, which specifically bind to PRSP, are useful as standards in assays for PRSP, such as by labeling purified PRSP for use as a standard in a radioimmunoassay, enzyme-linked immunoassay, or competitive-type receptor binding assays radioreceptor assay, as well as in affinity purification techniques. Ordinarily, the anti-PRSP antibody will bind PRSP with an affinity of at least about $10^6$ L/mole, and preferably at least about $10^7$ L/mole. The skilled person will readily be able to determine a suitable affinity. It will also be appreciated that if the antibody is an IgM it may be possible to use antibody of lower affinity.

For diagnostic applications, anti-PRSP antibodies typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, beta-galactosidase or horseradish peroxidase.

Any method known in the art for separately conjugating the antibody to the detectable moiety may be employed.

The anti-PRSP antibodies may be employed in any known assay method, such as competitive binding assays, direct and indirect sandwich assays, and immunoprecipitation assays.

Competitive binding assays rely on the ability of a labeled standard (e.g., PRSP or an immunologically reactive portion thereof) to compete with the test sample analyte (PRSP) for binding with a limited amount of antibody. The amount of PRSP in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. The second antibody may itself be labeled with a detectable moiety (direct sandwich assays) or may be measured using an anti-immunoglobulin antibody which is labeled with a detectable moiety (indirect sandwich assay). For example, one type of sandwich assay is an ELISA assay, in which case the detectable moiety is an enzyme.

The purposes of this specification it will be clearly understood that the word "comprising" means "including but not limited to", and that the word "comprises" has a corresponding meaning.

The invention will now be described in detail by way of reference only to the following non-limiting examples and drawings.

Example 1

Mice were genetically modified to render them null for the mouse gene encoding a long and short form serine protease (SEQ ID NO. 1 and 7) whose expression corresponds to proteins (SEQ ID NO. 2 and 8). Wild-type (+/+), heterozygous (+/−) and homozygous (−/−) female mice (approx 8 weeks old) were mated with males of the same strain. Pregnant mice were killed at day 18 of pregnancy (E18, the day before birth) and the fetuses and placentas weighed.

Overall, there was a significant decrease in fetal weight ($P<0.05$) in the fetuses derived from the −/− or +/−mothers compared with the +/+mothers (FIG. 1), while all three types of mothers had similar numbers of viable fetuses on E18.

Figure 2:
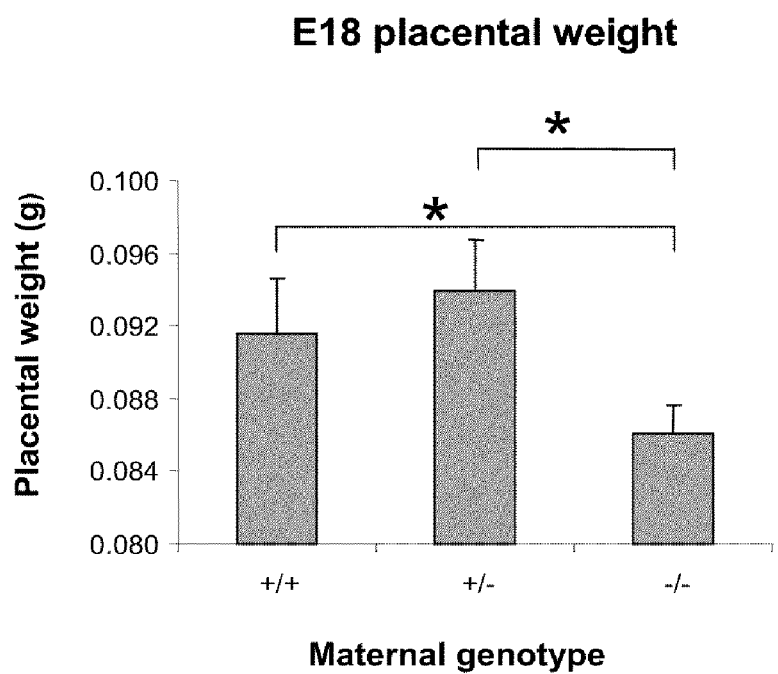
FIG. 2 shows the effects of maternal levels of the protease on placenta weight at E18.

There was also a significant decrease in placental weight ($P<0.05$) in the −/−mothers compared with the +/−mothers (FIG. 2).

Accordingly, deficiency of the serine protease shown in U.S. Ser. No. 10/485,313 to be upregulated at the site of embryo implantation in mothers; results in low birth weight fetuses and small placentas in mice. This supports the hypothesis that the protease is critical for placental development and function.

The null mouse provides a further model to study infertility conditions.

Example 2

Serum samples were taken from women between 7-9 weeks of pregnancy. All of these women delivered full-term babies without any obvious pregnancy complications. The women were separated into two groups according to the birth weight of their babies at term:
a) women gave birth to babies of normal birth weight (>3.3 kg) and
b) women gave birth to smaller babies (2.1-2.7 kg).

Figure 3:
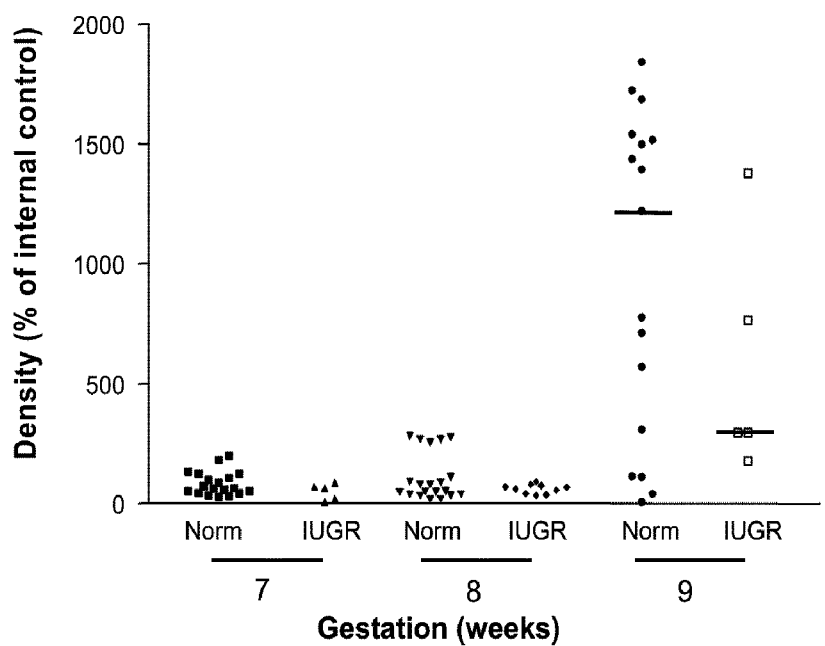
FIG. 3 shows serum levels of the protease (the 39 kD band) at 7-9 weeks of gestation.

Sera were subjected to Western blot analysis using an antibody specific for HtrA3 (raised against SEQ ID NO: 10). A band at 39 kDa was detected in all the sera; the density of the bands was lower at 7 and 8 weeks of pregnancy and increased dramatically at 9 weeks in both groups (FIG. 3). No difference in density was seen between the two groups at 7 weeks, at 8 weeks the density of the band was slightly lower in women who delivered smaller babies and the density of the band was much lower at 9 weeks of pregnancy in women who delivered smaller babies (FIG. 3) compared to control at 9 weeks.

These data strongly suggest that the lower levels of the protease in the maternal blood during first trimester are closely associated with higher risks of delivering a low-birth-weight baby at term. This supports the hypothesis that measurement of the expression of the serine protease between 8-15 weeks of pregnancy is diagnostic of IUGR.

Example 3

Serum samples were taken from women between 7-15 weeks of pregnancy and subsequently separated into two groups. a) women who underwent normal pregnancy and gave birth to healthy normal babies or b) women who subsequently developed pre-eclampsia (PE).

Figure 4:
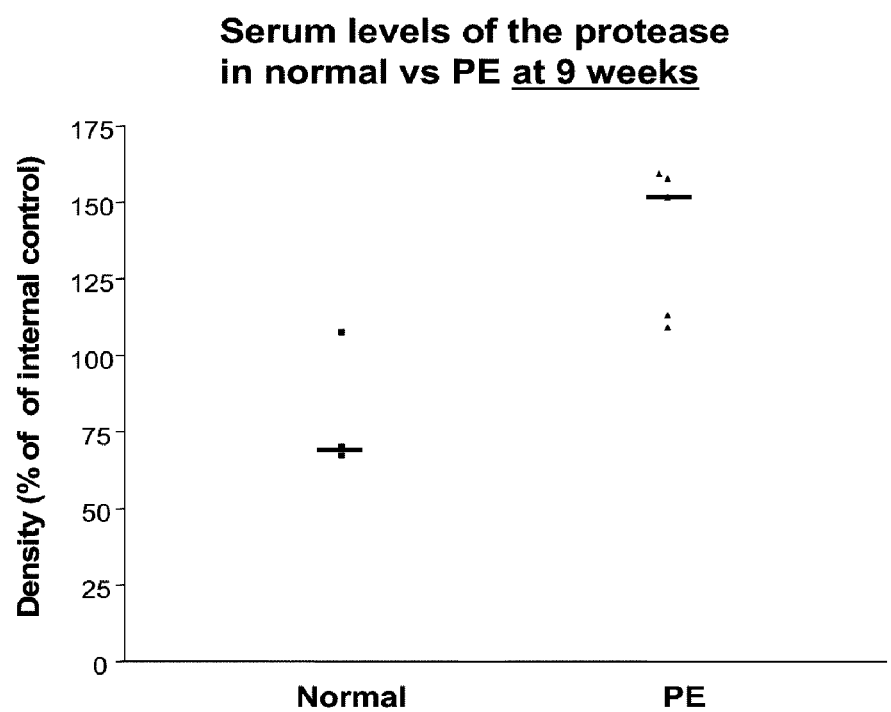
FIG. 4 shows serum levels of the protease (the 39 kD band) at 9 weeks of gestation.

Sera were subjected to Western blot analysis using the same antibody specific for HtrA3 as described in Example 2. A PRSP band around 39 kDa was detected in all the sera. At 9 weeks of pregnancy, the density of the PRSP band was significantly higher (P<0.05) in women who subsequently developed PE compared to the controls (FIG. 4).

Figure 6:
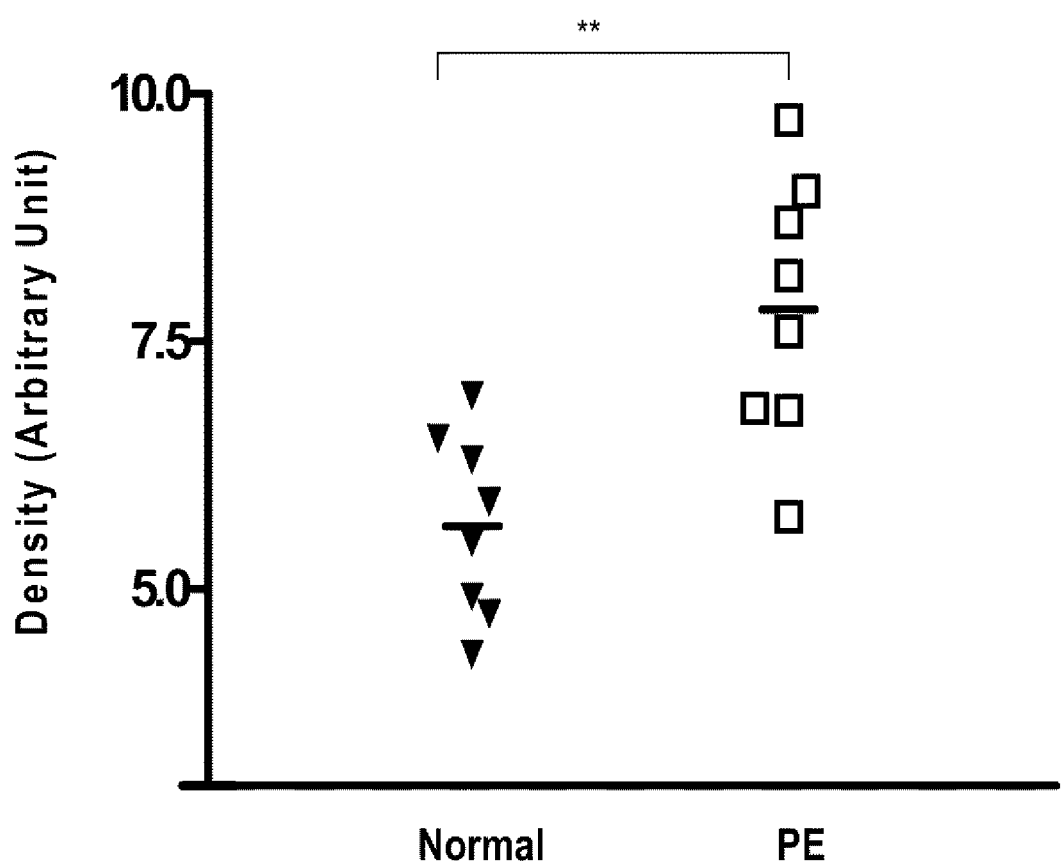
FIG. 6 shows serum levels of the protease (the 39 kD band) at 13-14 weeks of gestation.

The density of the 39 kDa PRSP band, the dominant band of PRSP, in the sera at 13-14 weeks of pregnancy are significantly higher in women who subsequently developed PE compared to the controls (FIG. 6).

Figure 5:
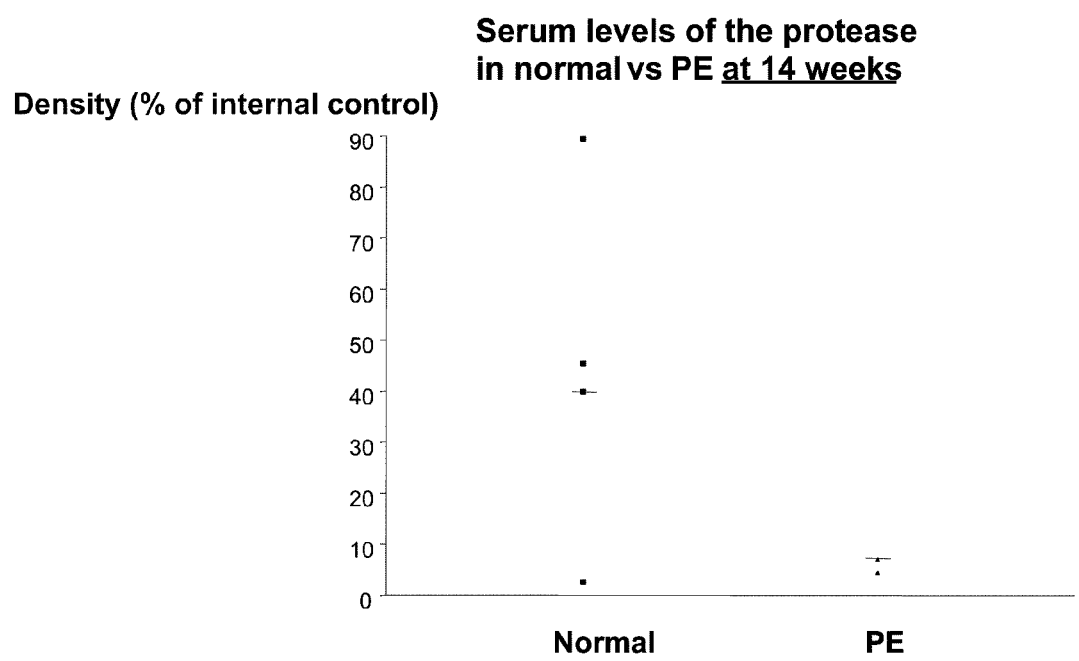
FIG. 5 shows serum levels of the protease (the 30 kD band) at 14 weeks of gestation.

At 14 weeks of gestation, another PRSP band at 30 kDa, in addition to the 39 kDa band, was detected, using the same antibody (raised against SEQ ID NO:10). The density of this 30 kDa PRSP band was much lower in women who subsequently developed PE compared to those who did not develop PE (FIG. 5).

The blood level of PRSP in first-trimester of pregnancy is different between women who subsequently develop or do not develop PE. This supports the hypothesis that measurement of the protease in the maternal blood during early stages of pregnancy may provide an early diagnostic test for PE.

These data provide strong evidence that monitoring PRSP in the maternal blood during early pregnancy may identify women who have higher risks of developing PE at later stages of pregnancy.

It is important to note that the measuring of the blood level of the protease at 9 weeks of gestation can differentiate between IUGR and PE conditions.

It is envisaged that PRSP levels will continue to distinguish IUGR and PE throughout early stage pregnancy.

Example 4

The cellular localization and expression levels of PRSP in the human placenta were determined by immuno-histochemistry on formalin fixed paraffin embedded samples using the same antibody as described above at 8-10 weeks ($1^{st}$ trimester), $2^{nd}$ trimester and at term. The localization and expression levels in the following cells was determined and shown in FIG. 7:

Syn, syncytiotrophoblast; cyt, cytotrophoblast; str, stroma; pro, proximal region of the anchoring villi; dis, distal region of the anchoring villi; mv, microvilli on the cells; shell, trophoblast shell; ed, endovascular trophoblast; deci, decidual cells; ge, glandular epithelial cell of the endometrium. The bar represents the overall decrease in expression levels of PRSP in the placenta as pregnancy proceeds.

Figure 7:
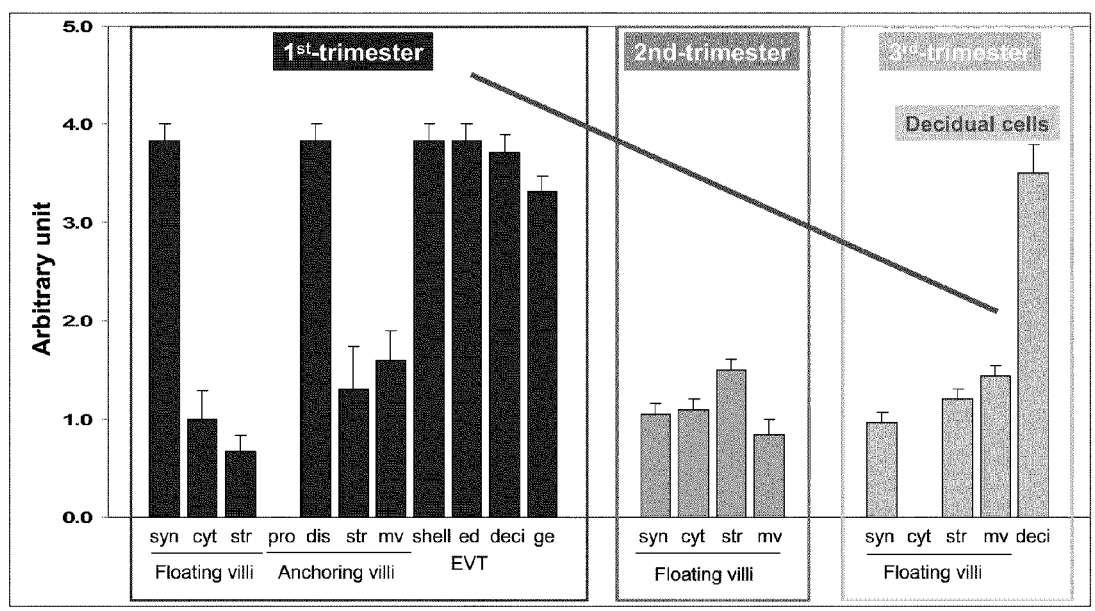
FIG. 7 shows cellular localization and expression levels of the protease in placental/maternal cells across gestation.

In the $1^{st}$ trimester placenta, PRSP was localized in floating villi, anchoring villi and extravillous trophoblasts. In the floating villi, PRSP was detected most strongly in the syncytiotrophoblast, whereas the levels in the cytotrophoblast and stroma were much lower. In the anchoring villi, PRSP was detected strongly in the distal region of the columns. In the extravillous trophoblasts, the trophoblast shell and endovascular trophoblasts were strongly positive for PRSP. In addition, the decidual cells and the glandular epithelium of the uterus were also strongly positive for PRSP (FIG. 7).

In the $2^{nd}$ trimester and term placenta, PRSP was detected mainly in the syncytiotrophoblast and the fetal capillary. The decidual cells at term were also strongly positive for PRSP.

The overall levels of PRSP protein in the placenta were much higher in the $1^{st}$ trimester of pregnancy.

Figure 8:
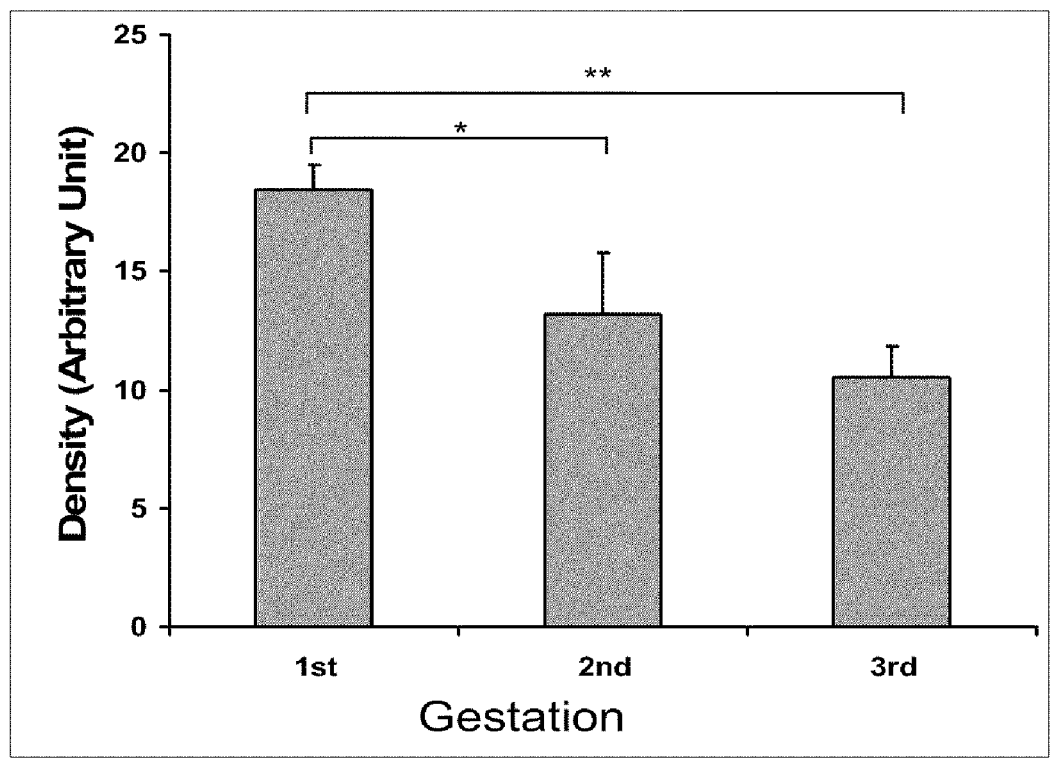
FIG. 8 shows serum levels of the protease in maternal blood across gestation.

The serum levels of PRSP were also determined at different times of normal pregnancy: 7-10 weeks ($1^{st}$ trimester), ($2^{nd}$ trimester) and term. The method of Western blotting was the same as the previous examples. The serum PRSP levels were highest in the $1^{st}$ trimester (FIG. 8). This indicates that the dynamic expression of PRSP in the placenta across gestation (FIG. 7) was reflected by a similar trend of change in the maternal blood. This supports the hypothesis that PRSP expression is important for placental development.

Example 5

Figure 9:
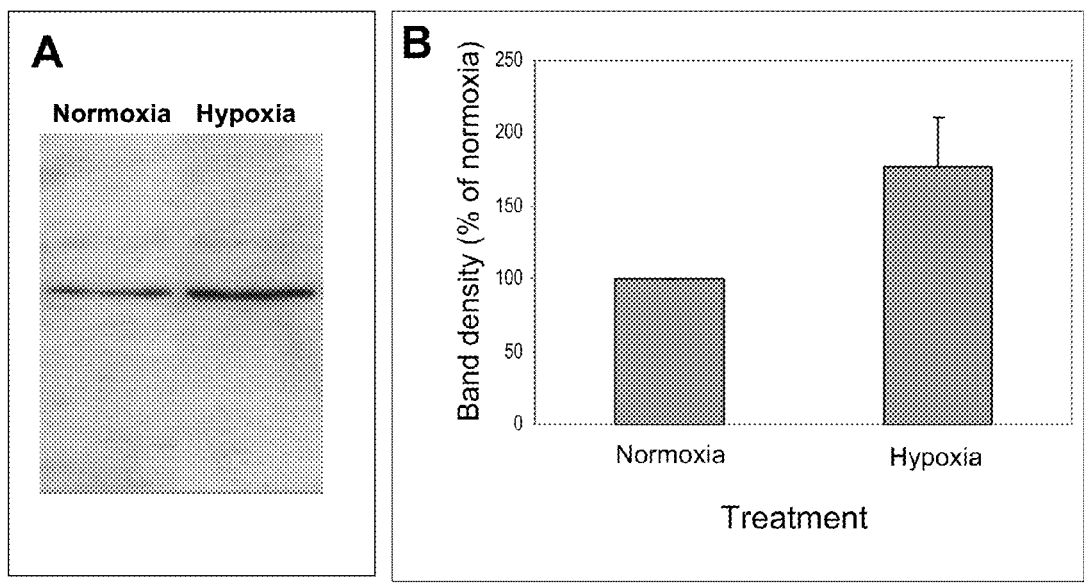
FIG. 9 shows protease levels in the media of explant culture of first trimester placenta.

Conditioned media from explant culture of $1^{st}$ trimester placenta (8-10 weeks) was assessed for PRSP. The placental tissues were cultured under normoxic (20% $O_2$) or hypoxic (5% $O_2$) conditions, PRSP levels in the media were determined by Western blotting as described above. PRSP levels were much higher in media from the hypoxic culture (FIG. 9) suggesting that PRSP is upregulated by hypoxic conditions.

Example 6

The cellular localization and expression levels of PRSP in term placenta from normal and PE pregnancy were determined by immuno-histochemistry as outlined in Example 4.

Figure 10:
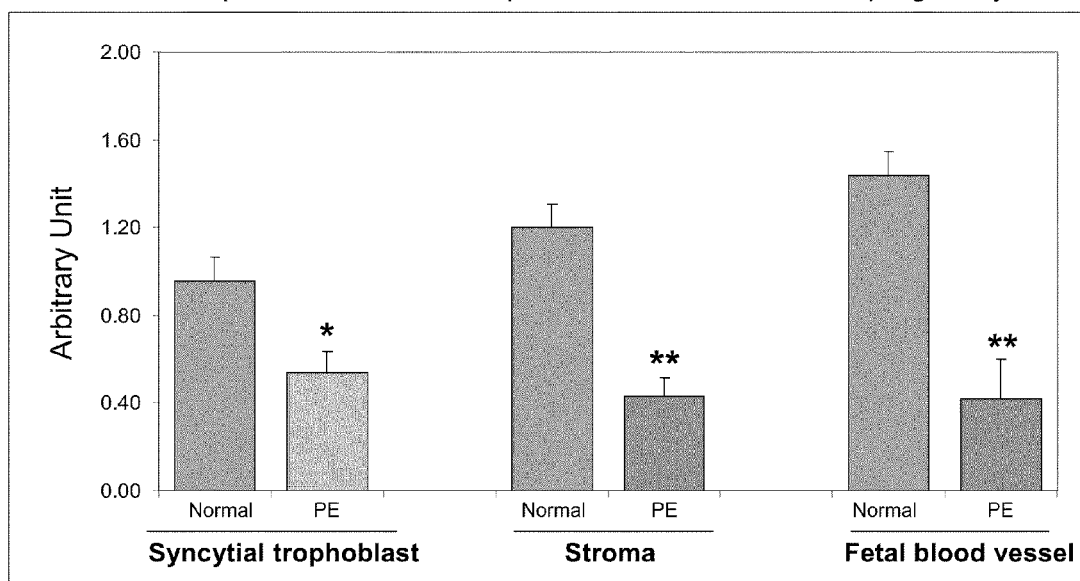
FIG. 10 shows protein levels of the protease in term placenta of normal and PE pregnancy.

PRSP was immunostained in the syncytiotrophoblast, villous stroma and fetal blood vessels in the floating villi. The overall intensity of the immunostaining was much weaker in the placenta from women with PE compared to normal pregnancy (FIG. 10). This supports the hypothesis that PRSP expression is important for placental development throughout pregnancy.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention claimed is:

1. A method of diagnosing an infertility condition in a human female subject in which the condition is pre-eclampsia or intrauterine growth restriction (IUGR), the method comprising (a) detecting pregnancy-related serine protease (PRSP) protein in a test sample taken from said subject at between 8 and 20 weeks into pregnancy;

(b) detecting PRSP protein in a control sample from a fertile control human female taken at the same number of weeks into pregnancy in the control as the sample taken from the subject; and (c) comparing the PRSP protein in the test sample with the PRSP protein detected in the control sample, wherein the PRSP protein comprises a sequence selected from the group of the sequences set out in SEQ ID NO: 2, 5, 6 or 8, in which a change in the PRSP protein in the test sample compared to the control sample is indicative of said condition.

2. The method of claim 1 in which the PRSP protein has the sequence set out in SEQ ID NO: 5 or SEQ ID NO: 6.

3. The method of claim 1 in which the PRSP protein is detected using an antibody.

4. The method of claim 3 in which the PRSP protein is detected using an antibody raised against a PRSP selected from SEQ ID NO: 2, 5, 6, 8 or a specific fragment thereof.

5. The method of claim 4 in which the PRSP protein is detected using an antibody raised against amino acids 133 to 142 of SEQ ID NO: 2 (SEQ ID NO: 9) or amino acids 116 to 126 of SEQ ID NO: 2 (SEQ ID NO: 10).

6. The method of claim 4 in which the PRSP protein is detected using an antibody raised against SEQ ID NO: 10.

7. The method of claim 1 in which the biological sample is a sample of biological fluid.

8. The method of claim 7 in which the biological fluid is plasma, serum, uterine or bladder washings or amniotic fluid.

9. The method of claim 1 in which the biological sample is a tissue or cellular sample or extract thereof.

10. The method of claim 9 in which the sample is placental or uterine tissue.

11. The method of claim 1 in which the test sample and the control sample are taken at around 8 weeks.

12. The method of claim 1 in which the test sample and the control sample are taken at around 9 weeks.

13. The method of claim 1 in which the test sample and the control sample are taken at around 10 weeks.

14. The method of claim 1 in which the test sample and the control sample are taken at around 11 weeks.

15. The method of claim 1 in which the test sample and the control sample are taken at around 12 weeks.

16. The method of claim 1 in which the test sample and the control sample are taken at around 13 weeks.

17. The method of claim 1 in which the test sample and the control sample are taken at around 14 weeks.

18. The method of claim 1 in which the test sample and the control sample are taken at around 15 weeks.

19. The method of claim 1 in which the PRSP protein is indicated by a 39 kDa band on Western blot using an antibody raised against SEQ ID NO: 10.

20. The method of claim 1 in which the PRSP protein is indicated by a 30 kDa band on Western blot using an antibody raised against SEQ ID NO: 10 and the test and control samples are taken at between 13 and 20 weeks into pregnancy.

21. The method of claim 20 in which the test and control samples are taken at between 13 and 14 weeks into pregnancy.

22. The method of claim 19 in which the change in PRSP protein is identified by a decrease in the density of the 39 kDa PRSP band indicative of IUGR.

23. The method of claim 19 in which the change in PRSP protein is identified by an increase in the density of the 39 kDa PRSP band is indicative of pre-eclampsia.

24. The method of claim 20 in which a decrease in the density of the 30 kDa PRSP band is indicative of pre-eclampsia.

* * * * *